United States Patent
Klingner

[11] Patent Number: 5,976,881
[45] Date of Patent: Nov. 2, 1999

[54] DEVICE AND METHOD FOR DETECTING CHEMICAL BREAKTHROUGH OF PROTECTIVE CLOTHING

[75] Inventor: Thomas D. Klingner, Prospect Heights, Ill.

[73] Assignee: Colormetric Laboratories, Inc., Des Plaines, Ill.

[21] Appl. No.: 07/890,620

[22] Filed: May 28, 1992

[51] Int. Cl.$^6$ .................................................. G01N 33/48
[52] U.S. Cl. .................................. 436/3; 436/1; 436/169; 422/58
[58] Field of Search ........................ 422/56–58; 436/1–3, 436/164, 169

[56] References Cited

U.S. PATENT DOCUMENTS

| | | |
|---|---|---|
| 1,623,510 | 4/1927 | Waggoner . |
| 2,156,880 | 5/1939 | Slomon . |
| 2,708,896 | 5/1955 | Smith et al. ............................. 422/56 |
| 2,762,711 | 9/1956 | Zopf, Jr. . |
| 3,516,846 | 6/1970 | Matson . |
| 3,520,124 | 7/1970 | Myers . |
| 3,552,929 | 1/1968 | Fields et al. ............................. 422/56 |
| 3,672,351 | 6/1972 | Ubersax et al. ........................ 422/56 |
| 4,473,079 | 9/1984 | Jasper et al. ............................. 422/56 |
| 4,643,588 | 2/1987 | Postle et al. . |
| 4,873,147 | 10/1989 | Jansen et al. . |
| 4,910,803 | 3/1990 | Cukier ..................................... 422/58 |
| 4,925,667 | 5/1990 | Fellows et al. . |
| 5,140,986 | 8/1991 | Klingner ................................ 128/636 |

*Primary Examiner*—Lyle A. Alexander
*Attorney, Agent, or Firm*—Emrich & Dithmar

[57] ABSTRACT

A detection device for testing gloves or other protective clothing or equipment for breakthrough by a contaminant includes a pad carrying a reagent which is responsive to the contaminant for producing a color change. A barrier layer covers the reverse side of the pad to prevent escape of chemicals therefrom and an adhesive strip is secured to the barrier layer for attachment of the pad either to the skin of the user or to the inside of the glove or other clothing so that the obverse side of the pad is adjacent to the inside of the glove. In one embodiment the pad is impregnated with the reagent which directly reacts with the contaminant to produce a color change. In another embodiment, plural reagents are carried respectively in separate regions of the pad and, after exposure to the contaminant, a carrier solvent is applied to the pad which brings the reagents into intimate contact for cooperation to produce the color change. In a third embodiment a substrate carries microcapsules of ink contained in shells soluble in a contaminant solvent, the pad also having a storage region for absorbing and storing the contaminant for later analysis. The obverse side of the pad may be covered with a semi-permeable barrier selectively permeable to the contaminant but impermeable to the reagents.

22 Claims, 2 Drawing Sheets

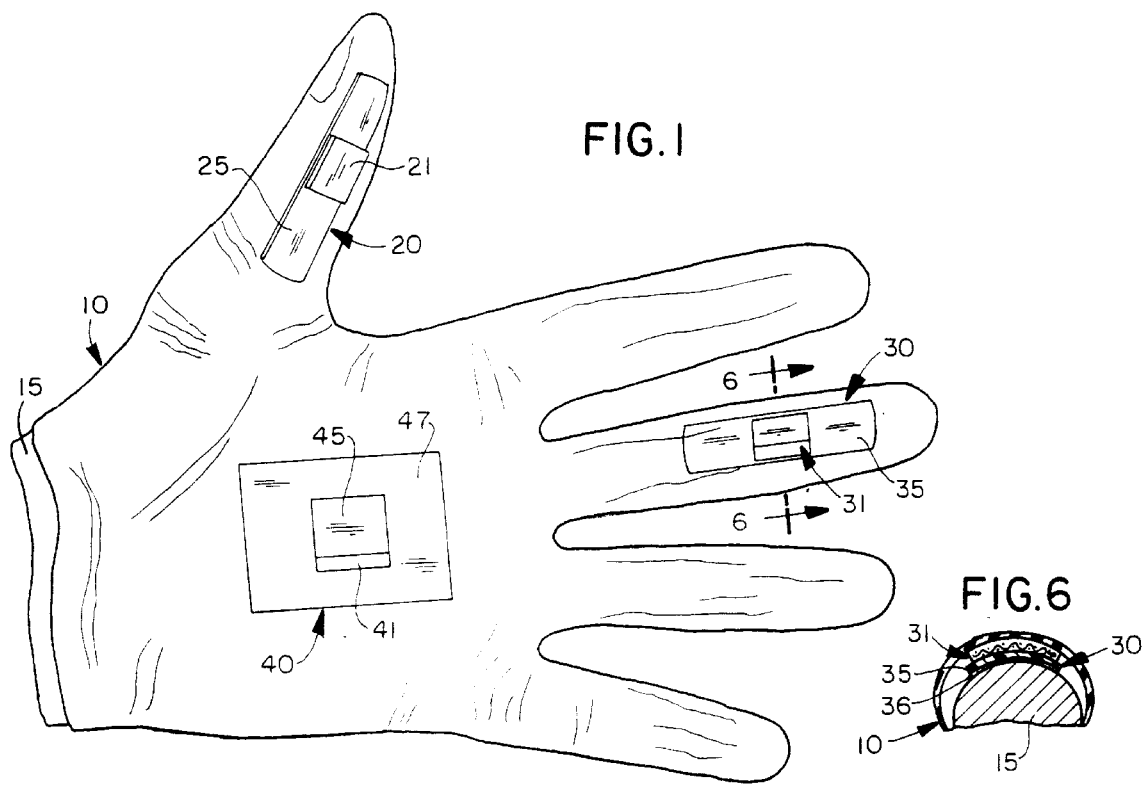
FIG. 1
FIG. 6
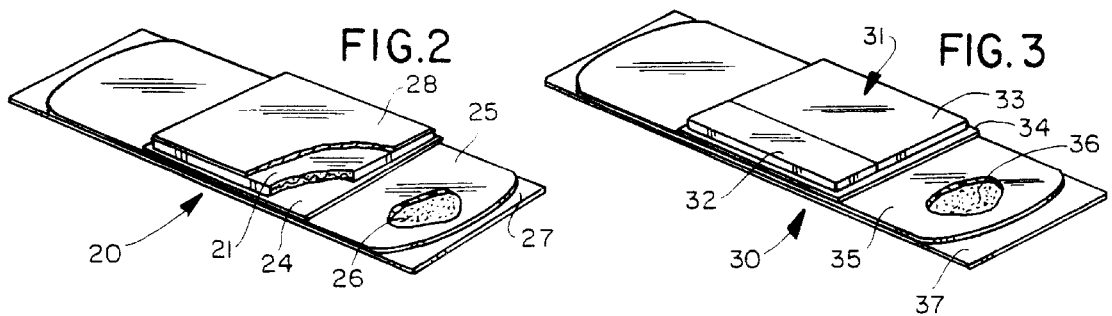
FIG. 2
FIG. 3
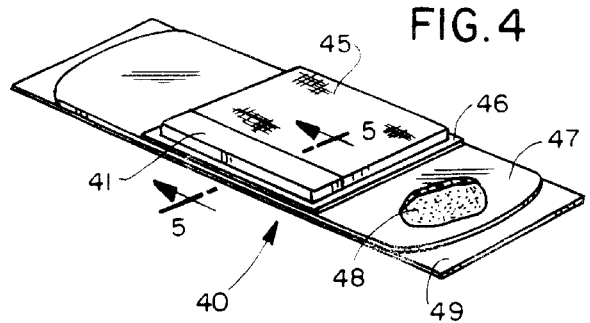
FIG. 4

DEVICE AND METHOD FOR DETECTING CHEMICAL BREAKTHROUGH OF PROTECTIVE CLOTHING

BACKGROUND OF THE INVENTION

1. Field of the Invention

The present invention relates to techniques for assessing the level of protection afforded by chemical resistant gloves and other protective clothing or equipment.

2. Description of the Prior Art

Health and safety organizations in the United States and foreign countries have historically regulated the allowable "safe" levels of chemical exposure in the workplace. Hundreds of compounds are variously listed in these countries with a "skin" designation which indicates the potential for considerable damage to the skin and/or systemic toxicity via dermal absorption. Accordingly, personal protective clothing and equipment is an important segment of safety in the workplace. One of the most common types of protective clothing is gloves designed to be resistant to contaminant chemicals of interest.

To date, the choice of chemical protective gloves and clothing has been based on laboratory testing of chemical breakthrough of the material of construction in accordance with test procedures specified by the American Society of Test Methods ("ASTM"). The ASTM distinguishes between "penetration", which it defines as the flow of a chemical through closures, porous materials, seams and pin holes or other imperfections in protective clothing material on a nonmolecular level, and "permeation", which it defines as the movement of a chemical through protective clothing material on a molecular level. The term "breakthrough" will be used herein as a generic designation encompassing both penetration and permeation. The ASTM test procedures specify that the protective material be tested for continuous exposure to the chemical or solvent system of interest. Such a test protocol is not a realistic representation of most field work situations, where chemical or solvent exposure most typically occurs on an intermittent and/or short-term basis. The result is that gloves or other protective clothing which pass the ASTM protocol for the chemical of interest are frequently overdesigned, i.e., they are much more resistant to the contaminant chemical of interest than is necessary for the particular field use application, and/or they are replaced much more frequently, in accordance with the protocol, than is necessary. This is costly and wasteful, since protective gloves and other clothing may be quite expensive to manufacture.

Another difficulty is that certain government regulations require the testing of gloves and other protective clothing to be based on the expected conditions of exposure, including the likely combinations of chemical substances to which the clothing may be exposed in the workplace, in order to establish that the clothing would be impervious for the expected duration and conditions of exposure. This required effectiveness of chemical protective clothing and gloves against combinations of chemical substances has been very difficult to ascertain in actual field use conditions. Thus, for example, protective gloves are made in a wide variety of different materials and different thicknesses for protection against different chemicals, and a glove which offers excellent protection for one chemical or group of chemicals may be completely unsuitable for protecting against a different chemical or group of chemicals. Prior efforts to measure chemical breakthrough of protective gloves and clothing have used cotton or cellulose pads attached under the gloves or clothing of absorb chemicals which break through the protective material. These pads are then analyzed in a laboratory to determine whether any breakthrough has occurred and, if so, to identify which chemicals have broken through the protective clothing. Then, the glove formulation is changed to one which is more protective against the penetrating chemical or chemicals and the test is repeated. But the requirement for laboratory testing to determine whether any breakthrough has occurred results in a significant additional expense, since laboratory analysis must be done every time.

SUMMARY OF THE INVENTION

It is a general object of the present invention to provide an improved breakthrough detection technique which avoids the disadvantages of prior techniques while affording additional structural and operating advantages.

An important feature of the invention is the provision of a device which affords an immediate in situ indication of breakthrough of protective clothing or equipment by a contaminant.

In connection with the foregoing feature, another feature of the invention is the provision of a device of the type set forth which is inexpensive and simple to use.

Another feature of the invention is the provision of device of the type set forth which detects breakthrough by any of a number of different contaminants.

Yet another feature of the invention is the provision of a device of the type set forth which permits selection of protective clothing or equipment based on actual field use conditions.

Another feature of the invention is the provision of a detection method incorporating a device of the type set forth.

These and other features are attained by providing a device for detecting the breakthrough of protective clothing or equipment by a contaminant, the device comprising: a reaction pad having obverse and reverse sides, reagent means carried by the reaction pad and responsive to the presence of the contaminant for producing a visible indication, a barrier layer impervious to the reagent means covering the reverse side of the reaction pad, and attachment means coupled to the reaction pad for mounting it so that the obverse side is adjacent to the inside of the protective clothing or equipment being tested.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there are illustrated in the accompanying drawings preferred embodiments thereof, from an inspection of which, when considered in connection with the following description, the invention, its construction and operation, and many of its advantages should be readily understood and appreciated.

FIG. 1 is a plan view of a gloved hand of a user having applied thereto detection devices in accordance with the present invention;

FIG. 2 is a perspective view of a breakthrough detector in accordance with a first embodiment of the invention, with portions broken away;

FIG. 3 is a view similar to FIG. 2, illustrating another embodiment of the invention;

FIG. 4 is a view similar to FIG. 3, illustrating yet another embodiment of the invention;

FIG. 6 is an enlarged, fragmentary sectional view taken along the line 6—6 in FIG. 1.

DESCRIPTION OF THE PREFERRED EMBODIMENTS

Figure 5:
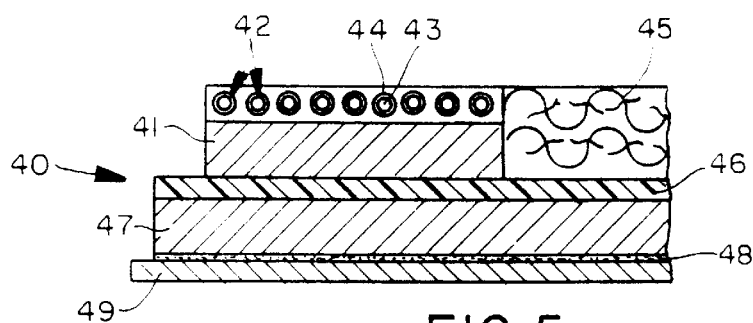
FIG. 5 is an enlarged, fragmentary sectional view taken along the line 5—5 in FIG. 4.

Referring to FIG. 1, there is illustrated a glove 10 disposed on the hand 15 of a user. To facilitate illustration, the glove 10 has been shown as formed of a transparent or translucent material, but it will be appreciated that it could also be opaque. There are illustrated on the user's hand 15 three breakthrough detectors 20, 30 and 40 in accordance with the present invention, respectively disposed on the user's thumb, middle finger and palm, for the purpose of detecting a predetermined contaminant chemical or chemicals being handled or used by the user, in the event that such chemical or chemicals break through the glove 10.

Referring now also to FIG. 2, the breakthrough detector 20 includes a reaction pad 21 which carries thereon a predetermined reagent or reagent system designed to be responsive to contact by the chemical or chemicals of interest to produce a visible indication, such as a color change. The reverse side of the reaction pad 21 is covered with a barrier layer 24 of a material which is impermeable to the reagent system and, preferably, also to the chemical or chemicals of interest. Affixed to the barrier layer 24 and extending therebeyond on opposite sides of the reaction pad 21 is an attachment strip 25 of a suitable material which is provided on one side thereof with an adhesive layer 26 and, preferably, is covered with a suitable peelable release liner 27 to protect the adhesive layer 26 when not in use. If desired, a semi-permeable barrier layer 28 may cover the obverse side of the reaction pad 21, the barrier layer 28 being formed of a material which is impermeable to the reagent system in the pad 21, but is permeable to the chemical or chemicals of interest.

The reaction pad 21 is formed of an absorbent material, which may be in the form of a woven fabric and may be composed of cellulose or cotton or a synthetic material, such as polyester, polypropylene or the like. Preferably, the reaction pad 21 is impregnated with a suitable detection reagent which is selected to react directly with the contaminant of interest or a product thereof to produce a color change. The barrier layer 24 may be formed of any suitable material which is impervious to a wide range of chemicals, such as polypropylene, polyethylene or PVC. The semi-permeable barrier layer 28 may be a microporous membrane formed of a suitable material, such as polyethylene, or may be formed of a hydrophobic material such as teflon, nylon or silicone, to prevent perspiration from entering the reaction pad 21. The attachment strip 25 may be formed of any suitable material, such as a woven material, and the adhesive layer 26 is any suitable peelable adhesive, preferably of the type which will adhere to both human skin and/or to the material of the glove or other protective clothing being tested.

In use, the release liner 27 is removed and the attachment strip 25 is adhesively secured to the skin of the user's hand in a selected location, such as any of those illustrated in FIG. 1, which is deemed most likely to come into contact with the contaminant of interest. Then, the glove 10 is put on the hand 15, so that the obverse side of the reaction pad 21 is adjacent to the inner surface of the glove 10, as illustrated in FIG. 6. Any contaminant which breaks through the glove 10 in the region of the breakthrough detector 20 will pass through the semi-permeable barrier layer 28 and into the reaction pad 21, where it then will react with the reagent or reagent system to produce the desired color change. This color change will be immediately apparent to a user in the event of a transparent or translucent glove. In the case of an opaque glove, the color change will be apparent when the glove is removed. The user will, therefore, know immediately if the glove 10 is either defective or it is not the proper material or thickness to afford adequate protection against the chemical contaminant of interest. The user will, also, immediately know that contaminant material may have made its way to the skin of the hand 15 and will know to clean the hand or take other indicated protective measures.

Referring to FIGS. 3 and 6, there is illustrated an alternative form of breakthrough detector 30, which is similar to the breakthrough detector 20 but has a multiple-component reagent system. In the detection of certain contaminant chemicals, more than a single reagent may be necessary, but the reagents may be incompatible, so that they must be stored in separately impregnated regions of the reaction pad. To this end, the breakthrough detector 30 includes a reaction pad 31 which has two separate reagent regions 32 and 33, which are, respectively, impregnated with different reagents. The reaction pad 31 may be formed of the same type of material as the reaction pad 21 described above. Preferably the two regions 32 and 33 are formed of the same material. Each is fabricated so as to facilitate a wicking action, whereby a liquid may be passed by capillary action from one to the other. The regions 32 and 33 may be formed of separate strips of material which are joined together in a suitable manner to form an integral reaction pad 31.

The reverse side of the reaction pad 31 is covered with a barrier layer 34, which serves the same purpose as the barrier layer 24 described above. Similarly, an attachment strip 35 is attached to the reverse side of the barrier layer 34 and projects therebeyond, being coated with an adhesive layer 36 and covered with a suitable release liner 37.

In use, the breakthrough detector 30 is applied to the user's hand 15 in the same manner as was described above in connection with the breakthrough detector 20. However, in this case, the breakthrough of the contaminant chemical of interest may not directly cause the color change. Since the reagents in the regions 32 and 33 are typically incompatible, preferably after the glove is removed, a suitable carrier solvent is applied to the reaction pad 31. The solvent is designed to activate one or both of the reagents in the regions 32 and 33 and to, through capillary action, bring the reagents into contact with each other for effecting the desired color change in the event that the chemical of interest has broken through to the reaction pad 31.

Referring to FIGS. 4 and 5, there is illustrated another breakthrough detector 40 in accordance with the present invention, which includes a substrate 41 formed of a suitable material, such as paper, having the obverse side thereof coated with a suitable coating of microcapsules 42. Each of the microcapsules 42 includes a liquid fill 43 contained within a shell 44, all in a known manner. It is a significant aspect of the present invention, that the shell 44 is formed of a material which is soluble in a contaminant solvent of interest, so as to release the liquid fill 43. Preferably, the liquid fill 43 is a suitable colorant, the color of which will become immediately apparent upon dissolution of the shell 44.

Preferably, the breakthrough detector 40 also includes a storage pad 45 formed of a suitable absorbent material designed to absorb the contaminant solvent of interest. Preferably, the substrate 41 and the storage pad 45 are arranged side by side, and their reverse sides are covered with a barrier layer 46 which may be of the same type described above in connection with the breakthrough detectors 20 and 30. The breakthrough detector 40 is also provided with an attachment strip 47 coated with a suitable adhesive 48 and provided with a release liner 49, all of which may be of the same types as described above in connection with the breakthrough detectors 20 and 30.

In use, the breakthrough detector 40 is applied to the user's skin in the same manner as was described above. In this case, when a contaminant solvent of interest breaks through the material of the glove 10 or other protective clothing being tested, it dissolves the shells 44 of the microcapsules 42, releasing the fill 43 thereof, which may be a suitable ink or dye to provide a visible indication of the breakthrough by the contaminant solvent.

The storage pad 45 is designed to absorb and store the contaminant solvent which has broken through the glove 10 for later analysis, such as in a laboratory. This feature is of particular importance when several contaminants or a contaminant mixture is used in the workplace. Specifically, the microcapsule shells 44 are formed of a material which is soluble in any of the contaminants which might be present in the mixture. Thus, in this case, when a color reaction occurs, the user will immediately know that a breakthrough has occurred, but he will not know which particular contaminant or contaminants have broken through and caused the reaction. Thus, the storage of the contaminant in the storage pad 45 permits its later analysis to identify the contaminant which has broken through.

It will be appreciated that the microcapsules 42 could be formed of varying diameters, and/or the shells 44 thereof could be formed of varying thicknesses, so as to vary the sensitivity of the microcapsules to the solvent or solvents of interest. In general, the sensitivity is directly proportional to the diameter of the microcapsules 42 and inversely proportional to the thickness of the shell 44.

While, in the embodiments illustrated in FIGS. 2–4, the adhesive layer is shown as covering the reverse side of the attachment strip, so that it can be attached to the skin of the user, it will be appreciated that, alternatively, it could be provided on the obverse side of the attachment strip. In that case, the breakthrough detector 20, 30 or 40 would be attached to the inside surface of the glove or other protective clothing being tested.

Figure 7:
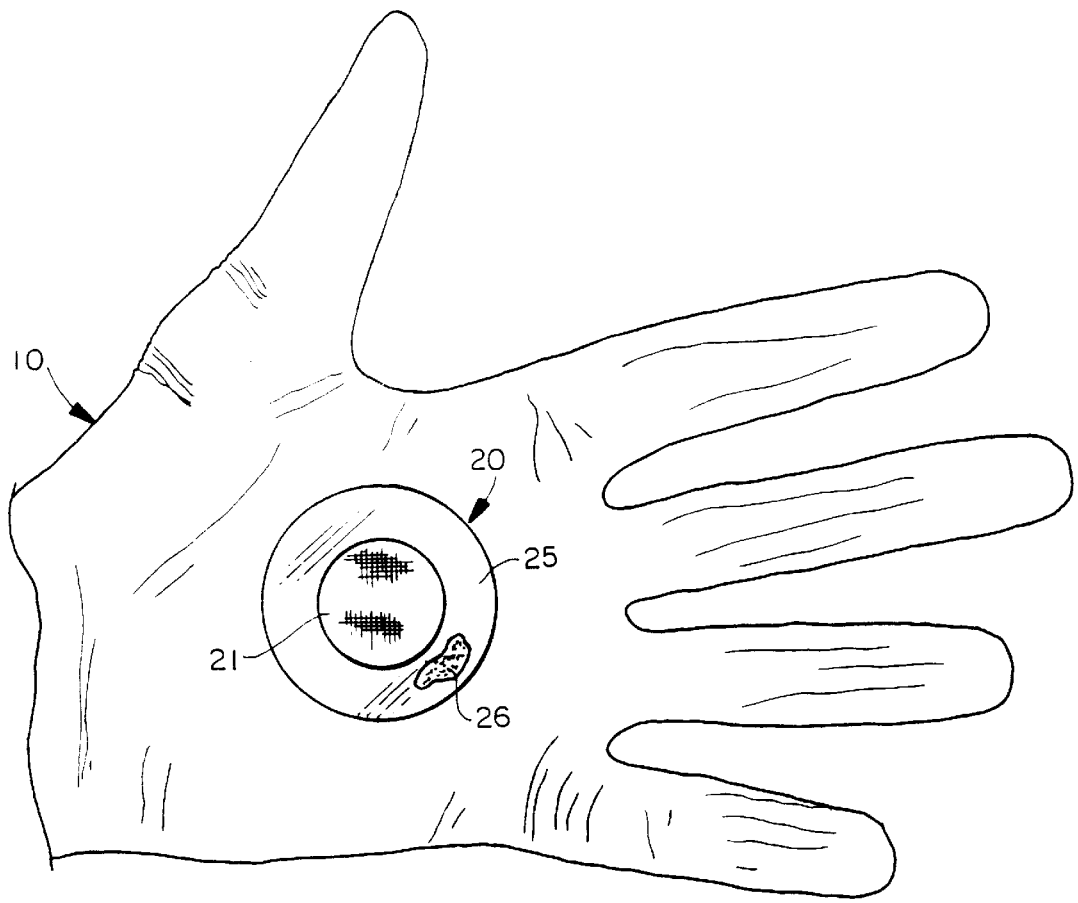
FIG. 7 is a view similar to FIG. 1, illustrating attachment of a detection device of the present invention on the outside of a glove.

Also, it will be appreciated that, if desired, any of the breakthrough detectors 20, 30, or 40 could be mounted on the outside of the glove or other protective clothing, as illustrated in FIG. 7. For example, in certain instances when testing a glove, particularly in the case of extremely toxic chemicals which might be harmful even in small quantities or even in the event of temporary contact with a user's skin, it is desirable for the user to first cover his hand with a glove of a known adequate protective capability. The breakthrough detector of the present invention is applied to the outside of that glove and, then, the glove to be tested is put on over the first glove carrying the breakthrough detectors.

While the breakthrough detectors 20, 30 and 40 and the reaction pads thereof have been illustrated as generally rectangular in shape, it will be appreciated that they could be formed in any desired shape or configuration, such as that shown in FIG. 7, for example.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure.

EXAMPLE I

Test for Aromatic Isocynates

A loosely woven polypropylene reaction pad 21 is impregnated with a solution of 2.0 gm naphthol AS as a color coupling reagent, along with 1.5 gm potassium acetate as a buffer and 1.25 gm sodium nitrite in 300 ml of methanol. The methanol is evaporated from the reaction pad 21 to leave a dry reagent system on the pad 21. The dry reagent system will react directly with aromatic isocynates which break through the glove 10 and reach the reaction pad 21 to form a colored compound in proportion to the amount of isocynate present.

In modifications of EXAMPLE I, the reagent system may incorporate a wide range of color coupling reagents other than naphthol AS. Also, other buffers or nitrite salts, such as potassium nitrite could be used, or solvents such as acetone. Additionally, other chemicals such as glycerine, polyethylene glycols, or diethyl phthalate may be incorporated into the reactant pad to facilitate the color reaction.

EXAMPLE II

Test for Aromatic Amines

One of the regions 32 and 33 of the reaction pad 31 is constructed as explained above for EXAMPLE I, while the other region is impregnated with an acid such as citric acid. In use, after the glove 10 is removed, the reaction pad 31 is wetted with water which dissolves the acid and the other reagent system and any collected aromatic amine. The acid/water solution and the reagent system solution in the regions 32 and 33 are then wicked by capillary action into contact with each other. The acid pH activates the stable chemicals in the reagent system, causing any aromatic amine present to diazotize and couple with the naphthol AS to create a color change. The amount of color formed is in proportion to the amount of aromatic amine contamination present.

In modifications of EXAMPLE II, the solvent may be an organic solvent, such as methanol or acetone. Also, other reagent systems, such as aromatic aldehydes or fluorescent reagents may be used for the detection of aromatic amines.

EXAMPLE III

Test for Benzene. Acetone or Methylene Chloride

The substrate 41 is constructed of paper. The microcapsules 42 comprise an ink fill contained within a shell 44 formed of gelatin with gum arabic and glutaraldehyde. This construction is commercially available as common thermal or facsimile paper. The storage pad 45 is formed of a charcoal cloth.

In use, if any of benzene, acetone or methylene chloride breaks through the glove 10 and contacts the microcapsules 42, it will dissolve the microcapsule shells 44 and release the ink fill to color the substrate 41.

In modifications of EXAMPLE III other materials can be used to construct the microencapsulation shell, including urea, formaldehyde polymer or other plastic encapsulants.

Additionally, the substrate 41 could be formed of other materials, such as cellulose, polypropylene, nylon, cotton and the like. The storage pad 40 may also be comprised of other absorbent materials such as silica gel or other man-made materials used to absorb chemical contamination.

I claim:

1. A device discrete from and usable with protective clothing or equipment worn by a user for detecting the breakthrough of the protective clothing or equipment by a contaminant, said device comprising: a reaction pad having obverse and reverse sides, reagent means carried by said reaction pad and responsive to the presence of the contaminant for producing a visible indication, a barrier layer impervious to said reagent means covering said reverse side of said reaction pad, and attachment means coupled to said reaction pad for removably mounting it between the user and the protective clothing or equipment being tested so that in use said obverse side is adjacent to the inside of the protective clothing or equipment for exposure to a contaminant which breaks through the protective clothing or equipment.

2. The device of claim 1, wherein said reagent means reacts with the contaminant to effect a color change.

3. The device of claim 2, wherein said reagent means includes means directly producing a color change upon contact with the contaminant.

4. The device of claim 1, wherein said reaction pad includes plural regions, and plural reagents respectively carried by said regions for cooperation to react with the contaminant to produce a visible indication.

5. The device of claim 4, wherein said reaction pad normally holds said reagents out of contact with each other, said reagents being soluble in a carrier solvent for cooperation to produce the visible indication in the presence of the contaminant.

6. The device of claim 1, wherein said reagent means is in the form of microcapsules.

7. The device of claim 6, wherein the contaminant is in the form of a solvent, each of said microcapsules including a liquid colorant contained within a shell of a material which is soluble in the contaminant solvent.

8. The device of claim 1, and further comprising a second barrier layer covering said obverse side of said reaction pad and impervious to said reagent means but permeable by the contaminant.

9. The device of claim 8, wherein said second barrier layer is hydrophobic.

10. The device of claim 1, wherein said attachment means includes an adhesive strip.

11. A device discrete from and usable with protective clothing or equipment worn by a user for detecting the breakthrough of the protective clothing or equipment by a contaminant solvent, said device comprising: a substrate, microcapsules carried by said substrate and each including a liquid colorant contained within a shell formed of a material which is soluble in the contaminant solvent, and attachment means coupled to said substrate for removably mounting it between the user and the protective clothing or equipment being tested so that in use said microcapsules are adjacent to the inside of the protective coating or equipment for exposure to a contaminant which breaks through the protective clothing or equipment.

12. The device of claim 11, wherein the liquid colorant is ink.

13. The device of claim 12, wherein the shell material is gelatin with gum arabic and glutaraldehyde.

14. The device of claim 11, wherein the substrate is paper.

15. The device of claim 11, wherein said attachment means includes an adhesive strip.

16. The device of claim 11, and further comprising a storage pad coupled to said attachment means for absorbing and storing the contaminant solvent.

17. The device of claim 16, wherein said storage pad is a charcoal cloth.

18. A method for detecting the break-through by a contaminant of protective clothing or equipment worn by a user, said method comprising the steps of: providing a pad having obverse and reverse sides and carrying a reagent responsive to the presence of the contaminant for producing a visible indication, sealing the reverse side of the pad to prevent escape of chemicals therefrom, and removably mounting the pad between the user and the protective clothing or equipment being tested so that the obverse side is adjacent to the inside of the protective clothing or equipment for exposure to a contaminant which breaks through the protective clothing or equipment.

19. The method of claim 18, and further comprising the step of partially sealing the obverse side of the pad to prevent escape of reagent therefrom while permitting the passage of the contaminant thereto.

20. The method of claim 18, and further comprising the step of applying an activating solvent to the reagent means to render it responsive to the contaminant.

21. The method of claim 20, and further comprising the steps of providing plural normally separated reagents on the pad, said reagents being joined by the activating solvent for cooperation to produce the visible indication in the presence of the contaminant.

22. The method of claim 18, and further comprising the step of storing contaminant on the pad.

* * * * *